United States Patent
Drozdz et al.

(10) Patent No.: US 9,586,875 B2
(45) Date of Patent: Mar. 7, 2017

(54) PROCESS FOR PURIFICATION OF OLEFINIC FEEDSTOCKS USING AN ADSORBENT COMPRISING A 12 MR-TYPE ZEOLITE

(71) Applicant: IFP Energies nouvelles, Rueil-Malmaison (FR)

(72) Inventors: Sophie Drozdz, Brindas (FR); Emmanuelle Bracco, Condrieu (FR); Delphine Marti, Lyons (FR); Elsa Jolimaitre, Lyons (FR); Arnaud Baudot, Vernaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 280 days.

(21) Appl. No.: 14/366,864

(22) PCT Filed: Oct. 31, 2012

(86) PCT No.: PCT/FR2012/000443
§ 371 (c)(1),
(2) Date: Jun. 19, 2014

(87) PCT Pub. No.: WO2013/093219
PCT Pub. Date: Jun. 27, 2013

(65) Prior Publication Data
US 2015/0005565 A1    Jan. 1, 2015

(30) Foreign Application Priority Data

Dec. 20, 2011 (FR) ..................... 11 03997

(51) Int. Cl.
| | |
|---|---|
| *C07C 7/12* | (2006.01) |
| *C07C 7/13* | (2006.01) |
| *B01J 20/18* | (2006.01) |
| *C10G 25/05* | (2006.01) |

(52) U.S. Cl.
CPC ............. *C07C 7/13* (2013.01); *B01J 20/18* (2013.01); *B01J 20/186* (2013.01); *C10G 25/05* (2013.01); *C10G 2300/1088* (2013.01)

(58) Field of Classification Search
CPC .................................. C07C 7/12; C07C 7/13
USPC ........................ 585/823, 824, 826
See application file for complete search history.

(56) References Cited

U.S. PATENT DOCUMENTS

| | | | |
|---|---|---|---|
| 2,882,244 A | * | 4/1959 | Milton ............. B01J 20/18 208/2 |
| 3,816,975 A | | 6/1974 | Collins |
| 5,834,392 A | | 11/1998 | Ramirez De Agudelo et al. |
| 5,858,211 A | | 1/1999 | Ramirez De Agudelo et al. |
| 5,880,052 A | | 3/1999 | Ramirez De Agudelo et al. |
| 8,530,367 B2 | | 9/2013 | Bouvier et al. |
| 2010/0113854 A1 | | 5/2010 | Bouvier et al. |

FOREIGN PATENT DOCUMENTS

FR      2903978 A1    1/2008

OTHER PUBLICATIONS

International Search Report for PCT/FR2012/000443 dated Oct. 15, 2013.

* cited by examiner

*Primary Examiner* — Thuan D Dang
(74) *Attorney, Agent, or Firm* — Millen White Zelano and Branigan, PC; John Sopp; Anthony Zelano

(57) ABSTRACT

The invention relates to a process for purification of olefinic feedstocks using an adsorbent comprising a 12 MR-type zeolite, in which the zeolite content of said adsorbent is between 93% by weight and 100% by weight, and the binder content of said adsorbent is between 0 and 7% by weight, in which said zeolite contains silicon and an element T that is selected from the group that consists of aluminum, boron, gallium and iron, and in which the Si/T atomic ratio is less than 20.

14 Claims, 1 Drawing Sheet

PROCESS FOR PURIFICATION OF OLEFINIC FEEDSTOCKS USING AN ADSORBENT COMPRISING A 12 MR-TYPE ZEOLITE

FIELD OF THE INVENTION

The invention relates to a process for purification of hydrocarbons using an adsorbent with reduced reactivity that has a very high zeolite content.

PRIOR ART

It is known to one skilled in the art that the molecules that contain heteroatoms (oxygen, sulfur, nitrogen, etc.) hamper the operation of a large number of industrial catalysts. Actually, these compounds are deposited on the active sites of catalysts that are then deactivated and are no longer active for catalyzing the reaction. Consequently, many patents recommend extracting these impurities from fractions before the catalytic reactors.

The most effective technique for extracting these impurities is the use of adsorbents that have a specific affinity for the impurities. The principle of the purification of feedstocks by adsorption is very simple. The fluid that is to be purified, for example a mixture of hydrocarbons, is injected into an adsorption column that contains an adsorbent that is placed in a fixed bed. In the column, the impurities are selectively adsorbed in the solid, which makes it possible to recover a purified fraction at the outlet. When the solid is saturated, its regeneration is initiated by circulation of a desorbent at high temperature. During this phase, the feedstock is directed toward another adsorption column.

The effectiveness of this type of process is greatly dependent upon properties of the solids that are used. Ideally, these solids should have:

A high adsorption capacity for the impurities that it is desired to extract.

Good regenerability (it should be possible to carry out the desorption of impurities under conditions of reasonable temperatures).

The longest service life possible. The adsorbents can actually lose their adsorption capacity over time. For example, they may not be stable enough thermally and may lose their mechanical properties during high-temperature desorption phases. The loss of capacity of adsorbents can also be caused by the formation of heavy carbon-containing products (coke) within their pores, causing a partial or total clogging of pores.

The size of the adsorbents used in the fixed beds is also a critical parameter. Actually, it is necessary that the adsorbent particles have a minimum size of approximately 0.5 mm so as to limit the losses of feedstock in the bed.

Relative to the purification of hydrocarbons, the zeolitic-type adsorbents have been identified for a long time as solids that have good performances. Owing to their polarity, they have a very strong affinity for the molecules that contain heteroatoms. Their adsorption capacity for these molecules is therefore very high, even in the presence of hydrocarbons. It is also possible to regenerate them at temperatures on the order of 300° C., which is perfectly applicable industrially. Finally, they have very good thermal stability.

It is commonly assumed that the zeolitic adsorbents have a major drawback: during successive cycles of adsorption and desorption, coke molecules form inside their pores and their adsorption capacity is reduced. This phenomenon is all the more critical since the feedstocks to be treated contain highly reactive molecules, called coke precursors, such as the unsaturated hydrocarbons. It is actually well known that the unsaturated molecules can react with one another to form more or less heavy oligomers as well as aromatic or polyaromatic molecules. This type of molecule cannot be extracted from the pores of the zeolites under normal regeneration conditions and will therefore be called coke below in this patent.

When it is a matter of purifying fractions containing unsaturated hydrocarbons, this problem is, of course, particularly critical. These fractions contain mono-unsaturated olefins and can also contain polyunsaturated molecules such as diolefins, which are coke precursors that are even more reactive than the mono-unsaturated olefins. Furthermore, the patents U.S. Pat. Nos. 3,816,975, 6,632,766, US 2002/0147377, and U.S. Pat. No. 5,271,835 teach that the co-adsorbed olefins with the impurities can be oligomerized in the pores of zeolites, which would be at the origin of the loss of performance of adsorbents over time.

In addition, the impurities themselves can be comprised in the same manner as coke precursors. It is well-known, for example, that the nitriles are very unstable groups and that the mercaptans can react with the olefinic molecules to form heavy sulfides.

So as to reduce this loss of adsorption capacity by coking, different approaches have been considered.

Certain proposals relate to improvements to be provided to the cyclic process. One approach that is considered in the patent U.S. Pat. No. 5,271,835 is to add hydrogen into the desorbent stream at a minimum concentration of 100 ppmv (parts per millions of volume). This addition of hydrogen would make it possible to minimize the coking reactions and therefore to maintain the capacity of the adsorbent during cycles.

It is also possible to avoid as much as possible heating the adsorbent when it is in contact with unsaturated molecules. Thus, the patent U.S. Pat. No. 3,816,975 proposes inserting an additional stage in the conventional adsorption/desorption cycle: after the high-temperature regeneration by a non-adsorbable gas, the bed is charged with saturated hydrocarbon prior to the injection of the olefinic feedstock. Thus, the increase in temperature caused by the adsorption of hydrocarbons takes place in the presence of less reactive molecules. This patent also teaches that the zeolites are responsible for coke deposits on the adsorbent.

Other patents focus rather on improving the formulation of the adsorbent, so as to make it less reactive. Thus, the patent U.S. Pat. No. 6,107,535 relates to the extraction of nitriles from a hydrocarbon fraction by selective adsorption on silica gels. The advantage of this type of material is that it is very sparingly acidic, which therefore makes it possible to prevent the formation of gums. In contrast, its adsorption capacity for the nitriles is high only when the concentration of these compounds in the feedstock is on the order of several thousand ppm. However, in the majority of cases, the concentration of nitriles in the olefinic fractions is much lower (less than 1,000 ppm). The adsorption capacity of the silica gels is then clearly lower than that of zeolites.

Since it is commonly assumed that the formation of coke is due to the excessive reactivity of the zeolite, other patents propose reducing the zeolite content in the adsorbent. The patents U.S. Pat. Nos. 5,834,392, 5,880,052, 5,858,211 and 6,019,887 propose using adsorbents that contain a non-acidic cationic zeolite mixture and an oxide-type inorganic matrix. The zeolite can selectively adsorb the nitriles whereas the inorganic matrix makes it possible to adsorb the dienes selectively and reversibly. In addition, the size of the pores of the zeolite is selected in such a way as to allow the nitriles to enter but to exclude the adsorption of the diolefins as much as possible. Thus, very few of the dienes enter the zeolitic cages and therefore cannot react with the active sites of the zeolites. The solid that consists of the zeolite and inorganic matrix mixture is preferably shaped using a binder. The use of this type of solid exhibits a major drawback: the adsorption capacity of the solid for the propionitrile is reduced. Actually, with neither the organic matrix nor the binder having a specific affinity for the nitriles, the adsorbent mass that is necessary for the purification of a given feedstock is therefore increased.

The patent U.S. Pat. No. 6,632,766 proposes using a shaped adsorbent that simultaneously contains a zeolite, an alumina oxide, and also a metal, preferably sodium. The addition of sodium makes it possible to reduce the reactivity of the adsorbent and more preferably to adsorb certain acid compounds such as $CO_2$ and COS. This adsorbent typically contains only 10 to 60% zeolite; its adsorption capacity for the polar and non-acidic impurities contained in the olefinic fractions is therefore greatly reduced. Furthermore, this patent as well as the patent U.S. Pat. No. 5,271,835 teach that the zeolites are responsible for the formation and the undesirable deposition of coke.

It therefore appears that the approaches proposed in the prior art are detrimental to the adsorption capacities of the solids that are used for the impurities and that according to the teaching of the prior art, the zeolites are responsible for the formation of coke precursors and for the deposition of coke.

We discovered, surprisingly enough, that a very large increase in the content of 12 MR-type zeolite in shaped adsorbents makes it possible to reduce the reactivity of said zeolite and therefore the formation of coke over time. The object of this patent is therefore to propose a process using a shaped adsorbent with reduced reactivity without loss of capacity with regard to the impurities.

SUMMARY OF THE INVENTION

The invention relates to a process for purification of a hydrocarbon feedstock comprising olefins containing one or more double bonds and impurities comprising at least one heteroatom, in which a stage for putting the feedstock into contact with an adsorbent is carried out, for example in the form of grains, comprising between 93% by weight and 99.8% by weight of zeolite and between 0.2 and 7% by weight of binder, with the zeolite being of the 12 MR type, in which said zeolite contains silicon and an element T selected from the group that consists of aluminum, boron, gallium, and iron, and in which the Si/T atomic ratio of the zeolite is less than 20.

DETAILED DESCRIPTION OF THE INVENTION

This invention describes a process for purification of hydrocarbons using a shaped adsorbent with reduced reactivity relative to unsaturated molecules.

The hydrocarbon feedstocks addressed by this invention contain unsaturated molecules. It may be a matter of olefinic molecules containing one or more double bonds or cyclic aromatic molecules. In general, the process according to the invention makes it possible to treat a hydrocarbon feedstock comprising olefins (i.e., hydrocarbon molecules comprising a double bond between two carbon atoms) and optionally diolefins (i.e., hydrocarbon molecules comprising at least two double bonds between two carbon atoms). There are no restrictions relative to the number of carbons of the molecules contained in these feedstocks, with the only condition being that the feedstocks should be liquid or gaseous at ambient temperature, so as to make possible the flow into the adsorbent beds.

The concentration of unsaturated molecules of the feedstocks according to the invention can be very diverse. Actually, with the unsaturated molecules being more polar than the saturated hydrocarbons, they are preferably adsorbed in the zeolitic adsorbents and can therefore bring about the formation of coke even if they are not very concentrated in the feedstock.

The treated hydrocarbon feedstock in the process according to the invention contains one or more impurities that are to be eliminated. The impurities contained in the feedstocks contain at least one heteroatom such as oxygen, nitrogen, and sulfur. According to the nature of the feedstock that is to be purified, the nature and the concentration of the impurities can very greatly vary. To illustrate this variability, we can present in detail the impurities that are encountered in different feedstocks of the refinery. For the C3-C4-type FCC fractions, the majority impurities are generally water, acetonitrile, acetone, methyl and ethyl mercaptan, DMDS, and COS.

For the raffinates of MTBE, the majority impurities are generally methyl and ethyl mercaptan, DMDS and DEDS, acetonitrile, acetone, methanol, ethanol, MTBE, TBA, and DME. For the C4 fractions of steam-cracking devices, the majority impurities are generally methyl and ethyl mercaptan, DMDS and DEDS, acetonitrile, DMF, NMP, and acetone. For the C5-C6 FCC fractions, the majority impurities will be C1-C3 mercaptans, thiophene, C2-C4 nitriles, and pyrrole.

The feedstocks of the processes according to the invention can contain variable polyunsaturated olefin contents. In particular, it is optionally possible to place the process according to the invention downstream from a selective hydrogenation process so as to reduce the content of polyunsaturated olefins in the feedstock.

The adsorbent according to the invention is for the most part composed of zeolitic crystals. The zeolite content of said adsorbent is generally between 93% by weight and 99.8% by weight, preferably between 94% by weight and 99.8% by weight, in a more preferred manner between 96% by weight and 99.8% by weight, and in an even more preferred manner between 97% by weight and 99.8% by weight.

The nature of the zeolite can vary according to the impurities that are to be adsorbed. Preferably, the adsorbent according to the invention comprises a zeolite whose pore diameter is large enough so that all of the impurities of the feedstock can penetrate into the porous network. The term pore diameter is conventional for one skilled in the art. It is used to define in a functional way the size of a pore in terms of the size of a molecule that is capable of entering into this pore. It does not indicate the actual dimension of the pore because the latter is often difficult to determine since it is often of an irregular shape (i.e., non-circular). D. W. Breck provides a discussion on the effective pore diameter in his book entitled Zeolite Molecular Sieves (John Wiley and Sons, New York, 1974) on pages 633 to 641. With the cross-sections of the channels of zeolites being rings of oxygen atoms, it is also possible to define the size of the pores of the zeolites by the number of oxygen atoms forming the annular cross-section of rings, designated by the term "member rings" or MR in English.

It is indicated in, for example, the "Atlas of Zeolite Structure Types" (W. M. Meier and D. H. Olson, 4th Edition, 1996) that the FAU-structural-type zeolites have a network of 12 MR crystalline channels, i.e., whose cross-section consists of 12 oxygen atoms. This definition is well known to one skilled in the art and will be used below. The zeolites that are characterized by the diameters of pores of at least 12 MR make possible the adsorption of many impurities and are therefore particularly suitable for our application.

Among the zeolites that contain channels of at least 12 MR and therefore in accordance with our invention, it is possible to cite the following families: AFI, AFR, BEA, EMT, FAU, LTL, and MOR.

Advantageously, the zeolitic adsorbents used in the process contain silicon and at least one element T that is selected from the group that is formed by aluminum, boron, gallium, and iron, preferably aluminum or gallium, and in a very preferred manner aluminum.

The silica content of these adsorbents can be variable. The Si/T atomic ratio of the zeolite according to the invention is preferably less than 20, in a more preferred manner less than 15, in an even more preferred manner less than 8, and in a very preferred manner less than 6, and even less than 5.

When the element T is aluminum, the Si/Al atomic ratio of the zeolite is preferably less than 8, in a more preferred manner less than 6, and in a very preferred manner less than 5, and even less than 4.

The zeolite that is contained in the adsorbent according to the invention is preferably exchanged with cations of elements selected from among the alkaline elements, the alkaline-earth elements, the lanthanides, or the transition metals. In a more preferred manner, said elements are selected from among the alkaline elements, the alkaline-earth elements, and the lanthanides; in an even more preferred manner from among the alkaline elements and the alkaline-earth elements; and in a very preferred manner from among the alkaline elements. Among the alkaline elements, sodium and potassium are preferred, and sodium is the alkaline element that is very preferred. Among the alkaline-earth elements, barium, magnesium, and calcium are preferred, and barium is the alkaline-earth element that is the most preferred.

According to a preferred variant of the invention, the zeolitic adsorbents are selected from among the family of FAU-type zeolites, which comprises, i.a., the following zeolites: X zeolite, Y zeolite, LSX zeolite. In an even more preferred manner, the FAU-type zeolite according to the invention is an X, Y or LSX zeolite.

Said FAU-type zeolite can be exchanged by any alkaline or alkaline-earth cation. According to a more preferred variant, the adsorbent according to the invention comprises an X- or Y- or LSX-type zeolite exchanged by sodium, potassium, or barium. In an even more preferred manner, the adsorbent according to the invention comprises a KX, NaX or BaX zeolite. In a very preferred manner, the adsorbent according to the invention comprises a KX or NaX zeolite, and in an even more preferred manner an NaX zeolite.

To synthesize the zeolite according to the invention, a gel is prepared by mixing—for example by means of a turbine—soda silicate, sodium aluminate, and water. The content of each of the reagents is adjusted based on the desired Si/Al atomic ratio. Curing of the gel is performed during a variable period at a temperature that is preferably close to 35° C., and then crystallization is performed at a higher temperature, preferably between 80° C. and 200° C. Next, the crystals are filtered and washed.

With the size of the zeolite crystals being on the order of magnitude of several micrometers, it is impossible to use them as such in industrial adsorbers, because the losses of feedstock that are generated would be much too high. It is therefore necessary to shape these crystals so as to form particles of greater size, i.e., on the order of a millimeter. These particles should, of course, have a great enough mechanical strength so as not to become deteriorated either during phases for charging the solid or by pressures exerted by the flow of fluids, or finally during heat regeneration stages.

The solids according to the invention can be shaped according to any shaping technique known to one skilled in the art, such as extrusion, granulation, or pelletizing. So as to reach mechanical strengths that are compatible with an industrial use, the addition of a binder during the shaping stage is necessary.

Actually, the zeolite crystals are not cohesive enough to be able to become agglomerated in the absence of binder, except in carrying out pelletizing at very high pressure, a shaping technique that is very cumbersome and able to bring about a partial amorphization of the zeolite and therefore a loss of capacity for the thus formed adsorbent.

Within the scope of the invention, any material that is added to the zeolite so as to shape it is called a binder. The binder rate of a shaped zeolitic solid is therefore the content by mass of any material other than the zeolite. The binder and the zeolite, taken in combinations, therefore represent 100% of the shaped zeolitic solid (also called adsorbent).

The mineral binder can preferably be selected from among clays, such as kaolin, the palygorskite-type minerals, such as attapulgite, and the smectite-type clay minerals, such as montmorillonite or bentonite. The binder can also consist of alumina or silica oxides. The binder preferably contains at least 70% clay; preferably said clay belongs to the family of kaolins, kaolinites, nacrite, dickite, halloysites and/or metakaolins. In an even more preferred manner, it contains at least 80% clay. During the shaping stage, additives can be added to the mixture of binder and zeolite so as to facilitate the agglomeration or to improve the mechanical strength of the particles. The particles obtained from the shaping procedure are to have adequate mechanical strength to be able to be used in an industrial process.

The preferred method for shaping the solid according to the invention consists in:
 a) Synthesizing a zeolite, according to any technique known to one skilled in the art,
 b) Shaping this zeolite using a binder, with a binder content that is preferably between 10 and 50% by weight. For example, the zeolite is mixed with the binder, and the mixture is shaped in the form of grains, for example balls, extrudates, or any other form.
 c) Initiating a zeolithization of grains obtained in stage b), i.e., a transformation of the binder into zeolite, a partial or total transformation of said binder, by any technique that is known to one skilled in the art. For example, the zeolithization is carried out by bringing grains into contact with a basic solution followed by a heat treatment. The binder content then reduces the zeolithization stage, with a portion of the binder being transformed into zeolite.

This method makes it possible to synthesize shaped solids that have a very high zeolite content and also that have mechanical properties that are compatible with the use in an industrial process. To evaluate the mechanical strength of the solids, the method for measuring grain-to-grain crushing (EGG) is used, which method consists in measuring the maximum compression force that a solid can withstand before it ruptures, when the product is placed between two planes moving at the constant speed of 5 cm/min. When it is a matter of extrudates, and therefore cylindrical solids, this force is related to the average length of the extrudates and is therefore expressed in terms of daN/mm. If it is a matter of balls, the EGG values are expressed directly in terms of daN. The mechanical strength of the adsorbent grains that is obtained can be greater than 0.4 daN/mm, preferably greater than 0.5 daN/mm, and even 0.6 daN/m, for extrudates, and greater than 1.5 daN, preferably greater than 2 daN, for balls.

During the zeolithization stage, the Si/T ratio is able to be modified. It is the Si/T ratio before zeolithization that is taken into account for the determination of the characteristics of the adsorbent. The Si/T ratio that is claimed is therefore determined before zeolithization and by means of any method of analysis known to one skilled in the art.

The zeolitic adsorbents according to the process of the invention have a binder content of between 0 and 7% by weight, preferably between 0.2 and 6% by weight, and in a more preferred manner between 0.2 and 4% by weight, and even between 0.2 and 3% by weight, of binder. Actually, we discovered that, surprisingly enough, the zeolitic adsorbents that contain more 12 MR zeolite not only have more capacity for the impurities of the hydrocarbon fractions but are also less reactive.

Different experimental methods that make it possible to estimate the binder content of a shaped solid are known to one skilled in the art. We can list the following methods, which are provided only by way of example and are not limiting:
 d) The X-ray diffraction (XRD). This method makes it possible to evaluate the relative quantities of amorphous phase (such as certain binders) and crystalline phase (such as zeolite) in a solid.
 e) The adsorption of different molecules. Under precise conditions of temperature and concentration, it is possible to measure the adsorbed quantities of a molecule simultaneously in the binder, in the zeolite, and in the shaped particle. It is then possible to deduce therefrom the binder content via the following formula:

$$x_{binder} = \frac{q_{zeolite} - q_{particle}}{q_{zeolite} - q_{binder}}$$

where $x_{binder}$ is the content by mass of binder, $q_{zeolite}$ is the concentration of adsorbed phase in the zeolite, $q_{particle}$ is the concentration of adsorbed phase in the particle, and $q_{binder}$ is the concentration of adsorbed phase in the binder. Of course, this method can be applied only when the concentrations of adsorbed phase are different for the zeolite and the binder.

A method derived from the preceding method consists in measuring the nitrogen adsorption isotherms at 77K of each of the three solids (zeolite, particle, binder), calculating the Dubinin volumes, the micropore volumes or the BET surface areas based on these isotherms, and determining the binder content by using the formula:

$$x_{binder} = \frac{P_{zeolite} - P_{particle}}{P_{zeolite} - P_{binder}},$$

where $P_i$ corresponds to any characteristic value that is obtained from the nitrogen adsorption isotherm (Dubinin volume, micropore volume, BET surface area, . . . ) for the solid i. Of course, this method can be applied only when the characteristic values obtained from the nitrogen adsorption isotherm are different for the zeolite and the binder.

The analysis of the chemical composition of the binder, of the zeolite (in particular during the determination of the Si/T ratio), and of the shaped particle, by any method of analysis known to one skilled in the art (analysis by X-ray fluorescence spectrometry, by atomic absorption spectometry). The binder content can then be evaluated by the formula:

$$x_{binder} = \frac{y_{zeolite} - y_{particle}}{y_{zeolite} - y_{binder}},$$

where $y_i$ corresponds to the content of any chemical element that is present in the solid $_i$. Of course, this method can be applied only when the chemical element contents are different for the zeolite and the binder.

Preferably, the binder rate of the adsorbents according to the invention is evaluated by the method of the Dubinin volume when this is possible. This method consists in an estimation of the micropore volume measured by nitrogen adsorption at 77 K by assuming that the Dubinin volume of the binder is zero. The Dubinin volume described above is calculated according to the Dubinin-Radushkevich equation, as described by Lowell et coll. (Characterization of Porous Solids and Powders: Surface Area, Pore Size and Density, Chapter 9, "Micropore Analysis," pages 143-145) and reproduced below:

$$\log V = \log V_o - D \cdot \log \frac{P^2}{P_o}$$

that connects the volume V of adsorbed nitrogen in the adsorbent material to the relative pressure $P/P_o$. The Dubinin volume is the volume $V_o$, maximum volume of nitrogen vapor that it is possible to condense in the micropores of the adsorbent material. It is expressed in terms of $cm^3$ of vapor (nitrogen) (converted to normal conditions) per gram of adsorbent.

Prior to the measurement, the sample is pretreated at 500° C. for 12 hours under vacuum ($P<5.10^{-6}$ Torr (or $6.7 \cdot 10^{-4}$ Pa)). The measurement is then made on an ASAP 2010 M-type device marketed by the Micromeritics Company. The adsorbate gas that is used is nitrogen. The trace of the isotherm is made using a pressure table of at least 35 points between 0.01 and 1 $P/P_o$. The value of log V is plotted on a diagram as a function of $(\log(P/P_o))^2$. The Dubinin volume is obtained from the ordinate at the origin of the straight line of linear regression of points of which $(\log(P/P_o))^2$ is between 1 and 2 (or $0.039<P/P_o<0.1$). The measurement uncertainty is ±0.003.

According to the composition of the feedstocks to be treated, it may be advantageous to use the adsorbent according to the invention in combination with other adsorbents. For example, when the feedstock contains water, it is possible to place a first layer of alumina in the column so as to extract water, followed by a second layer of adsorbent according to the invention so as to extract the other impurities. Likewise, when the feedstock contains nitrogen-containing and sulfur-containing molecules, the sulfur-containing molecules, which are less selectively adsorbed in the zeolites, have a tendency to be moved by the nitrogen-containing molecules. It may then be advantageous to place a selective adsorbent layer toward the sulfur-containing molecules upstream from the adsorbent layer according to the invention.

In the process according to the invention, the adsorbent can preferably be used in a stationary bed. For example, after having carried out the stage of putting the adsorbent into contact with the feedstock, putting the adsorbent into contact with the feedstock is stopped, and the following stages are carried out:
  i) The adsorbent is regenerated in such a way as to obtain an adsorbent that is low in impurities, and then
  ii) The collection mass that is low in impurities is brought into contact with said feedstock.

Preferably in stage i), the adsorbent is brought into contact with a regenerating fluid, with the regenerating fluid having a temperature that is higher than the temperature of the feedstock or the regenerating fluid having a pressure that is lower than the pressure of the feedstock.

According to a preferred variant, it is possible to use the adsorbent according to the invention by successively performing the following stages.
  a. Providing an olefinic feedstock comprising molecules containing heteroatoms
  b. Circulating the feedstock in a fixed bed containing at least one shaped adsorbent according to the invention
  c. Recovering the purified feedstock at the outlet of the fixed bed
  d. Bringing the adsorbent into contact with a regenerating fluid so as to desorb at least partially the molecules containing heteroatoms.

Then, stages b to d are repeated again.

According to a variant of the process according to the invention, the adsorbent according to the invention can be used according to the pressure modulation technique (PSA or Pressure Swing Adsorption according to English technology).

According to another preferred variant of the process according to the invention, the adsorbent is used according to the temperature modulation technique (TSA or Temperature Swing Adsorption according to English technology). It consists of different stages:
  1. Adsorption: The feedstock is injected into the adsorbent bed and the impurities are adsorbed in the bed; the feedstock exits in purified form from the column. This stage is carried out at a temperature of between 15 and 150° C., preferably 20 and 50° C.
  2. Movement of the feedstock through the desorbent: Stopping the injection of the feedstock in the column and injection of desorbent. The desorbent moves the feedstock that is present in the dead volumes of the column (interstitial and macro/mesopore volumes). This stage is carried out at the same temperature as Stage 1.
  3. Heating of the adsorbent bed by the desorbent, up to a final temperature of between 200 and 400° C., preferably 250 and 350° C. During this stage, the impurities are desorbed from the adsorbent.
  4. Cooling: gradual lowering of temperature in the column by injection of desorbent until the adsorption temperature is reached.
  5. Filling the column with the feedstock: stopping the injection of the desorbent and injection of the feedstock into the column. The column is ready for an adsorption stage.

This cycle is provided only by way of example, and the process according to the invention can also integrate additional stages, including intermediate stages located between stages 1 to 5.

According to the composition of the feedstocks to be treated, it may be advantageous to use the process according to the invention in combination with other purification techniques. In particular, it is possible to initiate washing the feedstock with water upstream from the purification process by adsorption according to the invention. Actually, certain polar impurities contained in the hydrocarbon fractions can be captured in large part in columns for extraction with water, and it may be economically advantageous to pair the two techniques.

EXAMPLES

Example 1

Figure 1:
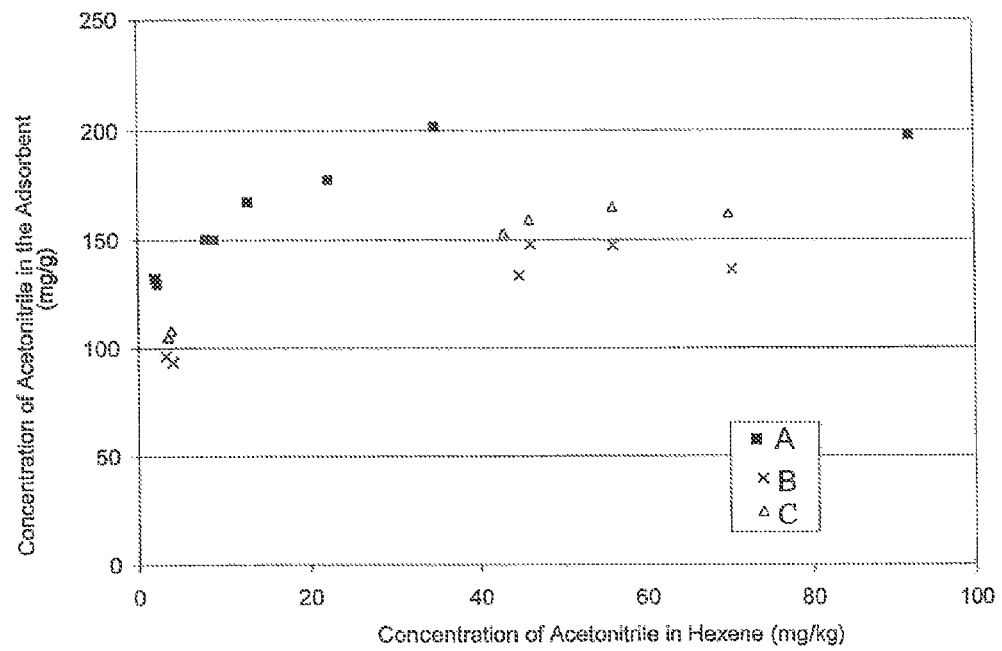
FIG. 1 shows that the adsorption capacity of acetonitrile by the adsorbent A according to the invention is greater than that of adsorbents B and C according to the prior art. The adsorbent A according to the invention therefore has a higher adsorption capacity while forming less coke.

Synthesis of Adsorbents A, B, C, and D

This example illustrates the reactivity of different adsorbents for the most part composed of the NaX zeolite: an adsorbent A according to the invention and two adsorbents B and C, not in accordance with the invention and representative of the prior art.

Synthesis of the Adsorbent A (According to the Invention):
a) Preparation of the Zeolite Powder:

A gel of molar composition 3.2 $Na_2O$-2.8 $SiO_2$-$Al_2O_3$-130 $H_2O$ is prepared by using the following reagents: soda silicate, sodium aluminate, and water. The gel is allowed to cure at 35° C. for 20 hours, and then crystallization is carried out for 4 hours at 100° C. Next, the powder containing zeolite crystals is filtered and washed. By XRD analysis, it is determined that these crystals belong to the faujasite family (FAU). The chemical analysis provides an Si/Al ratio=1.25+/−0.03.

b) Agglomeration:

Next, this zeolite powder is agglomerated by mixing it thoroughly with Charentes kaolinite and colloidal silica, with a ratio by mass of zeolite/kaolinite/silica of 12.3/2.3/1, with the masses of zeolite and kaolinite being weighed after calcination. Next, the extrudates are dried and calcined at 550° C. for 2 hours.

c) Zeolithization:

200 g of thus obtained extrudates is placed in a glass reactor equipped with a double jacket regulated at a temperature of 100° C., and then 1.5 liters of an aqueous soda solution of a 100 g/liter concentration is added, and the reaction medium is allowed to stir for 3 hours. Next, the particles are washed with water on three occasions before activating them at 350° C. under nitrogen.

Synthesis of the Adsorbent B (According to the Prior Art):
a) Preparation of the Zeolite Powder:
To synthesize the powder containing zeolite crystals of the adsorbent B, the operating procedure of stage a), described for the adsorbent A, is repeated.
b) Agglomeration:
The zeolite powder that is obtained in stage a) is agglomerated by mixing it thoroughly with Charentes kaolinite, with a ratio by mass of zeolite/kaolinite of 3/1, with the masses of zeolite and kaolinite being weighed after calcination. Next, the extrudates are dried and calcined at 550° C. for 2 hours.

No zeolithization stage is used during the synthesis of the adsorbent B.

Synthesis of the Adsorbent C (According to the Prior Art):
a) Preparation of the Zeolite Powder:
To synthesize the powder containing zeolite crystals of the adsorbent B, the operating procedure of stage a), described for the adsorbent A, is repeated.
b) Agglomeration:
Next, this zeolite powder is agglomerated by mixing it thoroughly with boehmite, with a ratio by mass of zeolite/boehmite of 4.56/1, with the masses of zeolite and kaolinite being weighed after calcination. The adsorbent C therefore does not contain silica. Next, the extrudates are dried and calcined at 550° C. for 2 hours.

No zeolithization stage is used during the synthesis of the adsorbent C.

Synthesis of the Adsorbent D (According to the Prior Art):
a) Preparation of the Zeolite Powder:
To synthesize the powder containing zeolite crystals of the adsorbent B, the operating procedure of stage a), described for the adsorbent A, is repeated.
b) Agglomeration:
The zeolite powder that is obtained in stage a) is mixed with boehmite, with a ratio by mass of zeolite/boehmite of 10.1/1, with the masses of zeolite and kaolinite being weighed after calcination. The agglomeration of the mixture has not taken place, and the extrusion therefore cannot be carried out. The solids that are shaped therefore cannot be synthesized.

No zeolithization stage is used during the synthesis of the adsorbent D.

The binder rate of the three adsorbents A, B and C was evaluated by the method of the Dubinin volume, which is an estimation of the micropore volume measured by nitrogen adsorption at 77 K by assuming that the Dubinin volume of the binder is zero. The Dubinin volume described above is calculated according to the Dubinin-Radushkevich equation:

$$\log V = \log V_o - D \cdot \log \frac{P^2}{P_o}$$

that connects the volume V of adsorbed nitrogen in the adsorbent material to the relative pressure $P/P_o$.

The Dubinin volume is the volume $V_o$, maximum volume of nitrogen vapor that it is possible to condense in the micropores of the adsorbent material. It is expressed in terms of $cm^3$ of vapor (nitrogen) (converted to normal conditions) per gram of adsorbent.

Prior to the measurement, the sample is pretreated at 500° C. for 12 hours under vacuum (P<5.10$^{-6}$ Torr (or 6.7·10$^{-4}$ Pa)). Next, the measurement is made on an ASAP 2010 M-type device marketed by the Micromeritics Company. The adsorbate gas that is used is nitrogen. The trace of the isotherm is made using a pressure table of at least 35 points between 0.01 and 1 $P/P_o$. A diagram bears the value of log V as a function of $(\log(P/P_o))^2$. The Dubinin volume is obtained from the ordinate at the origin of the straight line of linear regression of points of which $(\log(P/P_o))^2$ is between 1 and 2 (or 0.039<$P/P_o$<0.1).

The binder contents obtained for the three samples are specified in Table 1.

TABLE 1

Content of Binder and EGG of the NaX-Type Adsorbents

| | Binder Content (% by Mass) | EGG (daN/mm) |
|---|---|---|
| Adsorbent A (According to the Invention) | 5 +/− 2 | 0.9 |
| Adsorbent B (According to the Prior Art) | 24 +/− 3 | 0.8 |
| Adsorbent C (According to the Prior Art) | 19 +/− 3 | 0.8 |

In Table 1, it is also possible to note that the three adsorbents have EGG of greater than 0.6 and therefore compatible with use in industrial adsorbers.

Next, the reactivity of the three adsorbents A, B and C was tested as follows. Each adsorbent was activated under nitrogen at 400° C. for 2 hours. Next, 100 mg of adsorbent is transferred into a flask (of the vial type according to the English term) that contains 250 ml of pentadiene. The solid is kept in contact with the pentadiene for 15 hours. Next, approximately 30 mg of solid is sampled from said flask and placed in the nacelle of a SETARAM thermobalance under a helium stream of 3 Nl/h.

Next, temperature programming is applied in the scale, and, in parallel, the loss of mass of the sample is measured. In a first step, the temperature is kept at 30° C. for 60 minutes so as to evaporate the pentadiene that is condensed in the macropores. The sample is then heated to 500° C. with a gradient of 5° C./minute and then kept at 500° C. for 30 minutes. By always maintaining this same temperature, a gas that consists of half helium and half air is then injected into the thermobalance so as to burn the residual carbon for a period of 2 hours.

During the entire period of the experiment, the gaseous effluent at the thermobalance outlet is analyzed by a mass spectrometer, which makes it possible to differentiate the loss of mass caused by the desorption of pentadiene from that caused by the desorption or the burning of coke. Finally, the reactivity of the solid is evaluated by calculating the percentage of coke mass relative to the total desorbed mass.

The results that are obtained are noted in Table 2 below.

TABLE 2

Comparison of the Reactivity of Adsorbents A, B and C

| | % by Mass of Desorbed Pentadiene | % by Mass of Desorbed or Burned Coke |
|---|---|---|
| Adsorbent A (According to the Invention) | 73 | 27 |
| Adsorbent B (According to the Prior Art) | 64 | 36 |
| Adsorbent C (According to the Prior Art) | 57 | 43 |

The results of Table 2 show that upon contact with pentadiene, the solid according to the invention forms clearly less coke than the solids according to the prior art.

Example 2

Adsorption Capacity of Adsorbents A, B, and C

This example makes it possible to compare the adsorption capacities of the same samples as those defined in Example 1.

To do this, the samples are activated under nitrogen at 400° C. for 2 hours. Next, they are brought into contact in a flask (of the vial type according to the English term) with a hexene solution containing different concentrations of acetonitrile. Next, the flask is placed in a vibrating bath and thermostated at 30° C. for 24 hours. Next, the final acetonitrile content is analyzed by chromatography, which makes it possible to calculate by material balance the quantity of acetonitrile adsorbed in each of the adsorbents at different concentrations.

The results that are obtained are presented in FIG. 1.

FIG. 1 shows that the adsorption capacity of acetonitrile by the adsorbent A according to the invention is greater than that of adsorbents B and C according to the prior art. The adsorbent A according to the invention therefore has a higher adsorption capacity while forming less coke.

Example 3

Synthesis of Adsorbents E and F

This example shows that the reactivity of different adsorbents that are composed for the most part of KX zeolite: an adsorbent according to the invention and an adsorbent in accordance with the prior art [sic].

Synthesis of the Adsorbent E According to the Invention:
a) Preparation of the Zeolite Powder:

A gel with a molar composition of 3.2 $Na_2O$-2.8 $SiO_2$-$Al_2O_3$-130 $H_2O$ is prepared by using the following reagents: soda silicate, sodium aluminate, and water. The gel is allowed to cure at 35° C. for 20 hours, and then crystallization is performed for 4 hours at 100° C. Next, the crystals are filtered and washed. By XRD analysis, it is determined that these crystals belong to the family of faujasite (FAU). The chemical analysis provides an Si/Al ratio=1.25+/−0.03.

b) Agglomeration:

Next, this zeolite powder is agglomerated by mixing it thoroughly with Charentes kaolinite and colloidal silica, with a ratio by mass of zeolite/kaolinite/silica of 12.3/2.3/1, with the masses of zeolite and kaolinite being weighed after calcination. Next, the extrudates are dried and calcined at 550° C. for 2 hours.

200 g of thus obtained particles is placed in a glass reactor equipped with a double jacket regulated at a temperature of 100° C., and then 1.5 liters of an aqueous soda solution of a 100 g/liter concentration is added, and the reaction medium is allowed to stir for 3 hours. Next, the particles are washed with water on three occasions before they are activated at 350° C. under nitrogen.

Cationic Exchange:

Next, the extrudates are brought into contact with a 1.2N KCl solution for 1 hour in a rotavapor regulated to a temperature of 80° C. Next, the solid is recovered and then rinsed thoroughly with distilled water until the pH of the rinsing solution is equivalent to that of distilled water. Finally, the solid is dried in an oven at 100° C. during one night. The procedure for bringing the KCl in contact is repeated on three occasions so as to ensure the total exchange of cations.

Synthesis of the Adsorbent F (According to the Prior Art):
a) Preparation of the Zeolite Powder:

Synthesizing NaX zeolite crystals is begun according to the same operating procedure as for the adsorbent A according to the invention.

Cationic Exchange:

Next, the cationic exchange is initiated according to the procedure that is described for the adsorbent E above.

b) Agglomeration:

Next, this zeolite powder is agglomerated by mixing it thoroughly with Charentes kaolinite, with a ratio by mass of zeolite/kaolinite of 5.25/1, with the masses of zeolite and kaolinite being weighed after calcination. Next, the extrudates are dried and calcined at 550° C. for 2 hours.

The binder contents obtained for the three samples according to the method of the Dubinin volumes (cf. Example 1) are specified in Table 3.

TABLE 3

| Binder Content of the KX-Type Adsorbents | | |
|---|---|---|
| | Binder Content (% by Mass) | EGG (daN/mm) |
| Adsorbent E (According to the Invention) | 3 +/− 2 | 0.9 |
| Adsorbent F (According to the Prior Art) | 16 +/− 3 | 0.8 |

In Table 3, it is also possible to note that the two adsorbents E and F have EGG of greater than 0.6 and therefore compatible with use in industrial adsorbers.

Next, the reactivities of the two solids are tested according to the methodology explained in Example 1. The results that are obtained are noted in Table 4 below.

TABLE 4

| Comparison of the Reactivity of Adsorbents E and F | | |
|---|---|---|
| | % by Mass of Desorbed Pentadiene | % by Mass of Desorbed or Burned Coke |
| Adsorbent E (According to the Invention) | 77 | 23 |
| Adsorbent F (According to the Prior Art) | 68 | 32 |

The results noted in Table 4 show that the adsorbent according to the invention makes it possible to form less coke than the adsorbent according to the prior art.

Example 4

Adsorption Capacity of the Adsorbents E and F

This example makes it possible to compare the adsorption capacities of the samples that are synthesized in Example 3.

The experimental procedure is identical to the one described in Example 2.

Figure 2:
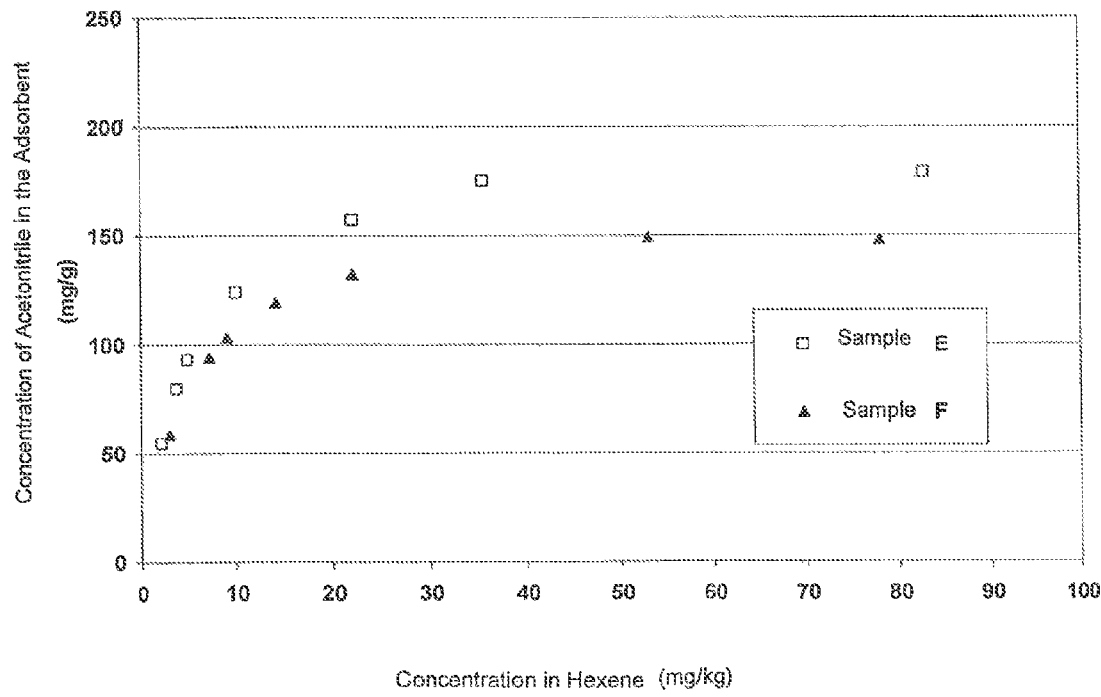
FIG. 2 shows that the adsorption capacity of acetonitrile by the adsorbent according to the invention is greater than that of adsorbents in accordance with the prior art. The adsorbent E according to the invention therefore has a higher adsorption capacity while forming less coke.

The results that are obtained are presented in FIG. 2.

FIG. 2 shows that the adsorption capacity of acetonitrile by the adsorbent according to the invention is greater than that of adsorbents in accordance with the prior art. The adsorbent E according to the invention therefore has a higher adsorption capacity while forming less coke.

Example 5

Synthesis of the Adsorbent G (According to the Prior Art)

This example illustrates the necessity for adding a binder for imparting adequate mechanical strength to the shaped particles.
a) Preparation of the Zeolite Powder:
The first step is to synthesize the NaX zeolite crystals according to the same operating procedure as for the adsorbent A according to the invention.
b) Shaping:
The pelletizing of the NaX zeolite crystals is done using a press of the Korsch brand (EKO model). The lower punch that has a hole with a diameter of 3.5 mm makes it possible to shape the zeolite crystals in the form of pellets with a diameter of 3.5 mm. The filling shoe of the press is filled with NaX crystals, and compacting is initiated with the following parameters: die with 15 mm of depth, depth of penetration of the punch equal to 11 mm, speed of rotation of the rotor equal to 25 rpm, dimensions of each pellet: diameter equal to 3.5 mm, thickness equal to 4 mm.

At the end of the pelletizing procedure, the NaX pellet is very friable and crumbles at the moment it is extracted from the shoe of the press. The NaX powder therefore cannot be shaped without a binder by pelletizing; the mechanical strength of the thus formed particle is inadequate.

The invention claimed:

1. Process for purification of a hydrocarbon feedstock comprising olefins and at least one impurity comprising at least one heteroatom:
   wherein the process comprises a stage for bringing the feedstock into contact with an adsorbent,
   wherein, before said contacting, the adsorbent has been obtained by:
   a) providing a zeolite,
   b) mixing the zeolite with a binder and shaping the resulting mixture in the form of grains, with the mixture comprising between 10% and 50% by weight of binder,
   c) conducting zeolithization of the grains obtained in b),
   wherein the adsorbent comprises between 93% by weight and 99.8% by weight of zeolite and between 0.2 and 7% by weight of binder, the zeolite is of the 12 MR type, the zeolite contains silicon and an element T selected from the group that consists of aluminum, boron, gallium and iron, and in which the Si/T atomic ratio of the zeolite, calculated before conducting the zeolithization, is less than 20.

2. Process for purification according to claim 1, in which the Si/T atomic ratio of the zeolite, calculated before conducting the zeolithization, is less than 15.

3. Process for purification according to claim 1, in which said element T is aluminum or gallium.

4. Process for purification according to claim 1, in which the element T is aluminum.

5. Process for purification according to claim 4, in which the Si/Al atomic ratio of the zeolite is less than 8.

6. Process for purification according to claim 1, in which said zeolite is exchanged with cations of elements selected from among the alkaline elements, the alkaline-earth elements, the lanthanides, or the transition metals.

7. Process for purification according to claim 1, in which said zeolite is selected from the group that consists of the zeolites AFI, AFR, BEA, EMT, FAU, LTL, and MOR.

8. Process for purification according to claim 1, in which said zeolite is a KX or NaX zeolite.

9. Process according to claim 8, in which said zeolite is an NaX zeolite.

10. Process for purification according to claim 1, in which said binder contains at least 70% clay.

11. Process for purification according to claim 1, in which the adsorbent is in the form of an extrudate and has a mechanical strength that is greater than 0.4 daN/mm, with the mechanical strength being determined by the method for measuring grain-to-grain crushing (EGG).

12. Process for purification according to claim 1, in which the adsorbent is in the form of a ball and has a mechanical strength that is greater than 1.5 daN, with the mechanical strength being determined by the method for measuring grain-to-grain crushing (EGG).

13. Process for purification according to claim 1, in which after the contact stage,
   i) the adsorbent is regenerated in such a way as to obtain an adsorbent that is low in impurities, and then
   ii) the adsorbent that is low in impurities is brought into contact with said feedstock.

14. Process for purification according to claim 13, in which in stage i), the adsorbent is brought into contact with a regenerating fluid, the regenerating fluid having a temperature that is higher than the temperature of the feedstock or the regenerating fluid having a pressure that is lower than the pressure of the feedstock.

* * * * *